(12) United States Patent
Fox et al.

(10) Patent No.: US 11,872,512 B2
(45) Date of Patent: Jan. 16, 2024

(54) ROBOT AIR FILTER

(71) Applicant: XTEND AI Inc., Middleburg, FL (US)

(72) Inventors: Harry Fox, Jerusalem (IL); Sergh Sapojnikov, Ashkelon (IL); David Azoulay, Jerusalem (IL); Andrew C. Gorelick, Ashkelon (IL); Gabriel Bachman, Sderot (IL)

(73) Assignee: XTEND AI Inc., Middleburg, FL (US)

( * ) Notice: Subject to any disclaimer, the term of this patent is extended or adjusted under 35 U.S.C. 154(b) by 0 days.

(21) Appl. No.: 18/167,857

(22) Filed: Feb. 12, 2023

(65) Prior Publication Data
US 2023/0264133 A1 Aug. 24, 2023

Related U.S. Application Data

(60) Provisional application No. 63/483,981, filed on Feb. 9, 2023, provisional application No. 63/327,836, filed
(Continued)

(51) Int. Cl.
B01D 46/00 (2022.01)
B01D 46/10 (2006.01)
(Continued)

(52) U.S. Cl.
CPC ............... B01D 46/46 (2013.01); A61L 9/20 (2013.01); B01D 46/0028 (2013.01);
(Continued)

(58) Field of Classification Search
CPC ........ B01D 50/00; B01D 46/10; B01D 46/46; B01D 46/0028; B01D 46/0041;
(Continued)

(56) References Cited

U.S. PATENT DOCUMENTS 7,094,142 B1 * 8/2006 Maskell .................... F24F 8/10
454/251
7,108,731 B2 * 9/2006 Park ......................... A47L 7/04
55/400
(Continued)

FOREIGN PATENT DOCUMENTS

CN 106403106 A 2/2017
CN 206080397 U 4/2017
(Continued)

OTHER PUBLICATIONS

International Search Report for corresponding application PCT/US23/62448 dated May 10, 2023.
(Continued)

Primary Examiner — Minh Chau T Pham
(74) Attorney, Agent, or Firm — HEIDI BRUN ASSOCIATES LTD.

(57) ABSTRACT

An intelligent robot includes at least one accessory to measure activity and state in proximity to the robot; an air filtration module housed in a casing made of a UV blocking material; and a control center to analyze output of the at least one accessory, to recognize a known target user according to the analysis and to control functionality of said robot and the air filtration module for said known target user according to saved preferences for said known target user.

3 Claims, 14 Drawing Sheets

Related U.S. Application Data on Apr. 6, 2022, provisional application No. 63/313,317, filed on Feb. 24, 2022.

(51) Int. Cl.
  *B01D 46/46* (2006.01)
  *A61L 9/20* (2006.01)

(52) U.S. Cl.
  CPC ......... *B01D 46/0041* (2013.01); *B01D 46/10* (2013.01); *A61L 2209/111* (2013.01); *A61L 2209/12* (2013.01); *A61L 2209/14* (2013.01); *B01D 2273/30* (2013.01); *B01D 2279/65* (2013.01)

(58) Field of Classification Search
  CPC ............. B01D 2273/30; B01D 2279/65; B25J 9/1666; B25J 9/1684; B25J 13/089; B25J 9/162; A61L 9/20; A61L 2009/12; A61L 2009/14; A61L 2009/111
  USPC .................. 55/318, 356, 385.1, 400, DIG. 3, 55/DIG. 34; 15/319, 340.1, 347; 180/218
  See application file for complete search history.

(56) References Cited

U.S. PATENT DOCUMENTS

| | | | | |
|---|---|---|---|---|
| 10,207,296 | B2* | 2/2019 | Garcia | B07C 5/34 |
| 11,000,613 | B1 | 5/2021 | Kellogg, Jr. et al. | |
| 11,203,120 | B1* | 12/2021 | Hill | B25J 9/0087 |
| 2010/0047115 | A1* | 2/2010 | Krichtafovitch | A61L 9/16 422/4 |
| 2010/0206651 | A1* | 8/2010 | Nagasaka | B25J 5/007 180/218 |
| 2016/0263266 | A1 | 9/2016 | Wesen | |
| 2019/0085852 | A1 | 3/2019 | Brown et al. | |
| 2019/0120518 | A1 | 4/2019 | Kim et al. | |
| 2019/0381661 | A1* | 12/2019 | Taira | B25J 9/162 |
| 2020/0355379 | A1* | 11/2020 | Kim | F28F 13/125 |
| 2020/0361715 | A1* | 11/2020 | Meier | F16N 9/00 |
| 2021/0252712 | A1* | 8/2021 | Patrick | G05D 1/0212 |
| 2021/0299311 | A1 | 9/2021 | Yu | |
| 2021/0354945 | A1* | 11/2021 | Deng | B25J 19/023 |
| 2021/0394930 | A1 | 12/2021 | O'Toole | |
| 2022/0347859 | A1 | 11/2022 | Fox et al. | |
| 2023/0107624 | A1* | 4/2023 | Keith, Jr. | G06F 21/32 704/249 |

FOREIGN PATENT DOCUMENTS

| | | |
|---|---|---|
| CN | 214074367 U | 8/2021 |
| CN | 114043489 A | 2/2022 |
| CN | 216159257 U | 4/2022 |
| KR | 1021070052743 A | 5/2017 |
| WO | 2021194023 A1 | 9/2021 |

OTHER PUBLICATIONS

Combined Search and Examination Report for corresponding application GB22067383 dated Jun. 28, 2022.

Examination Report for corresponding application GB22067383 dated Aug. 25, 2022.

* cited by examiner

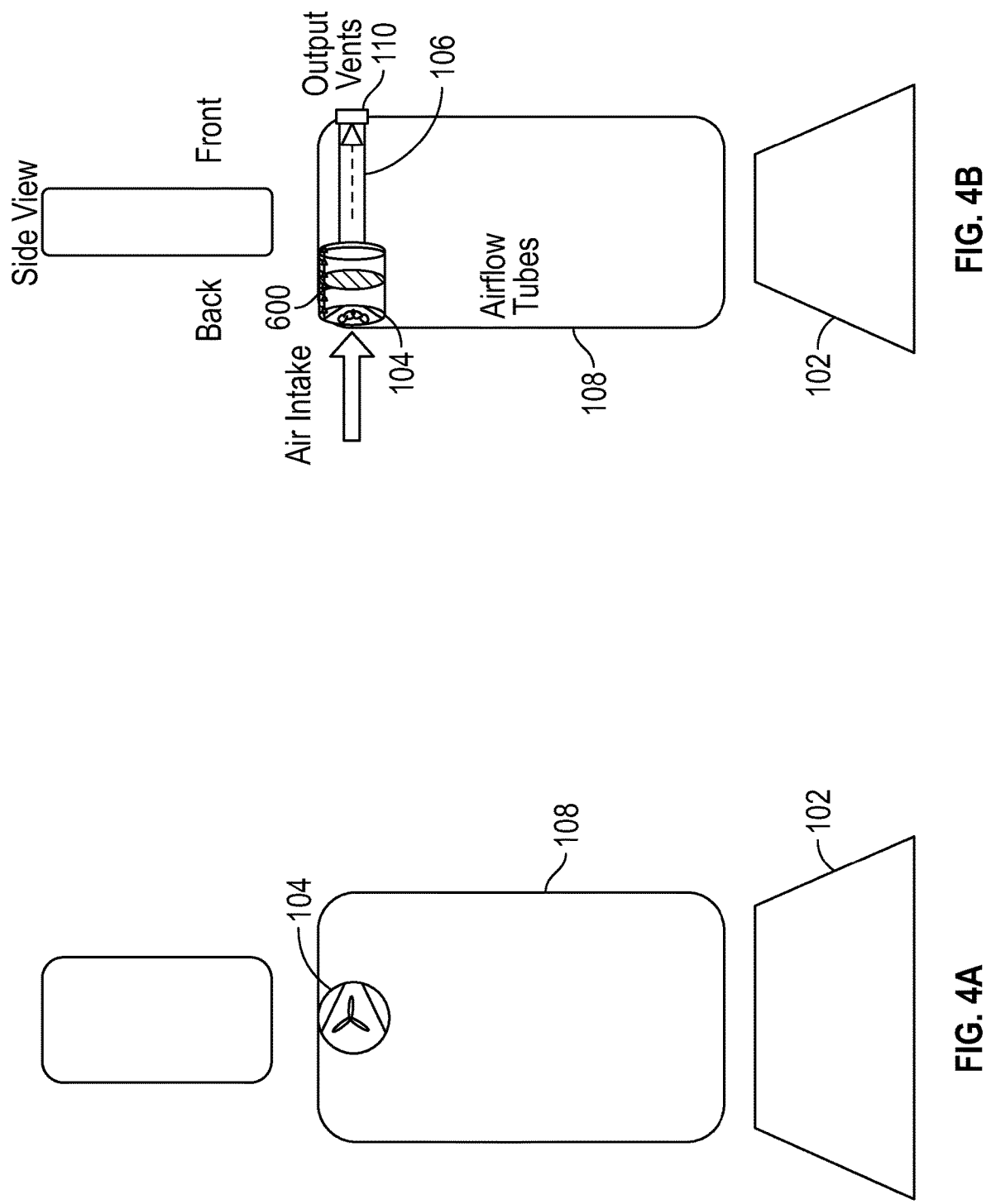

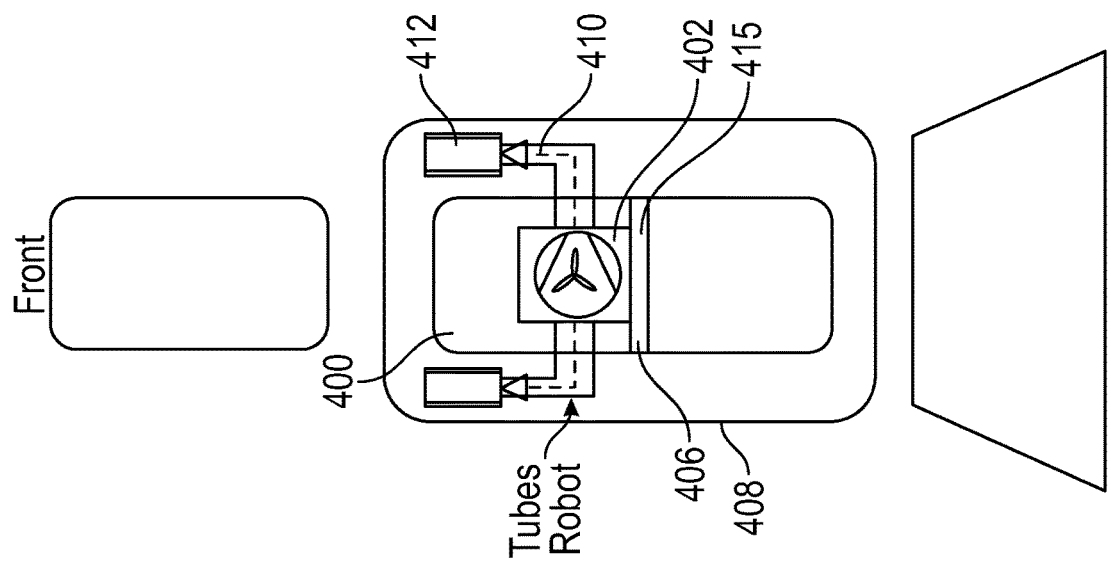
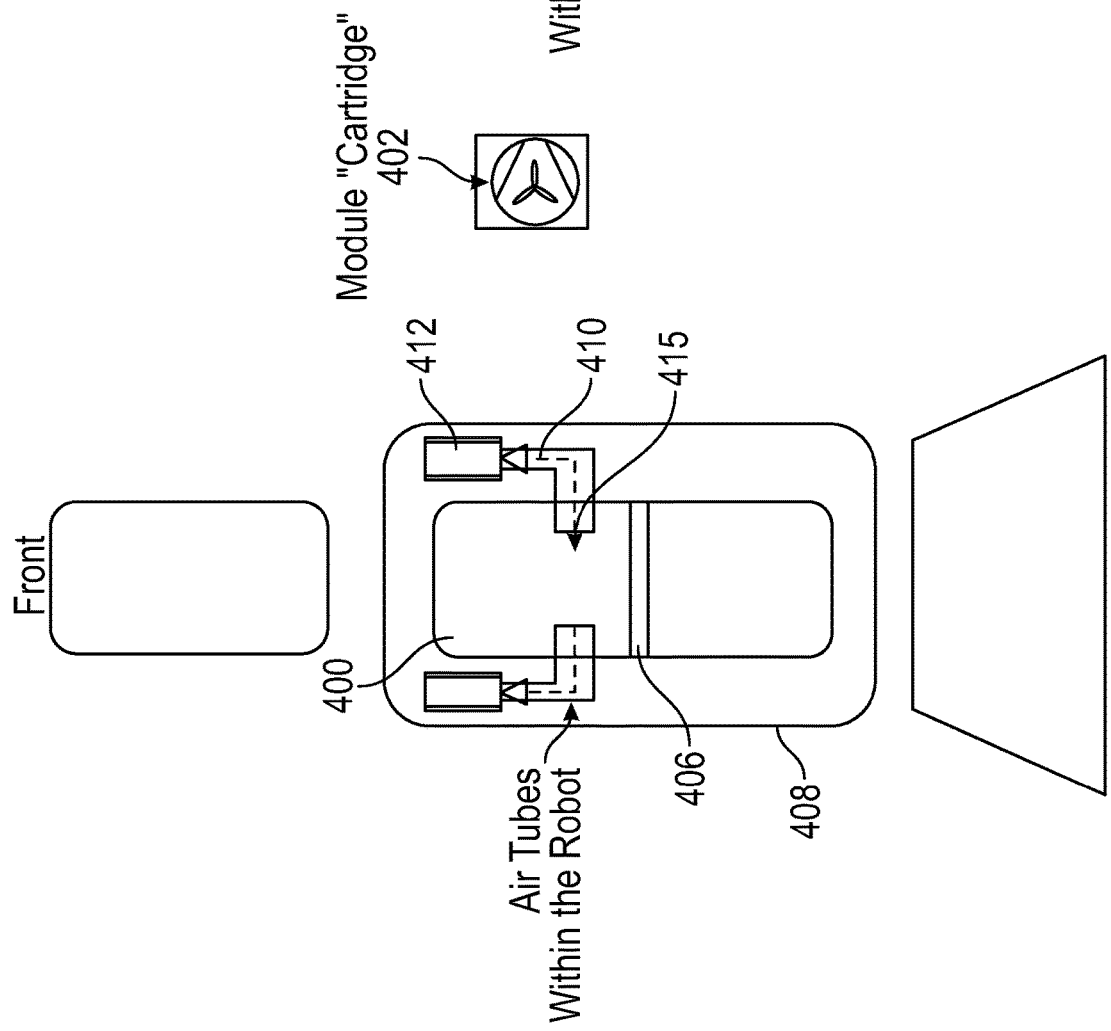
FIG. 5C
FIG. 5D

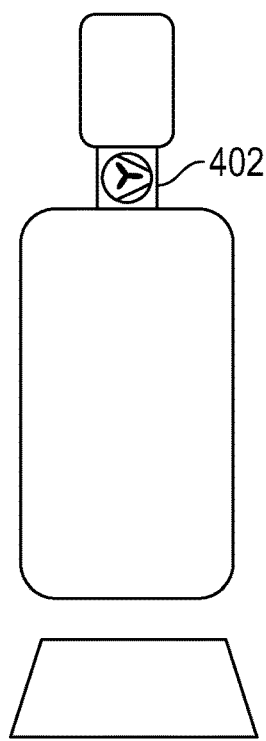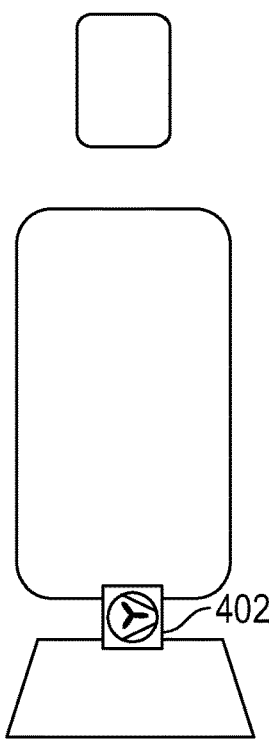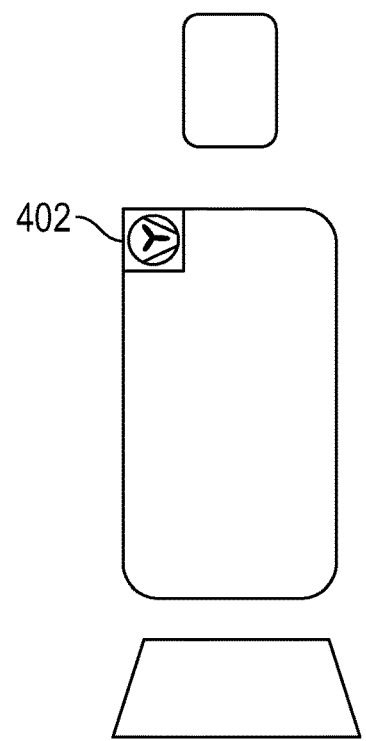
FIG. 6A　　　　FIG. 6B　　　　FIG. 6C
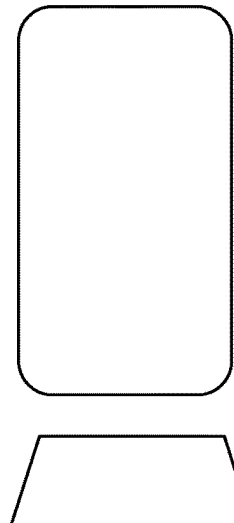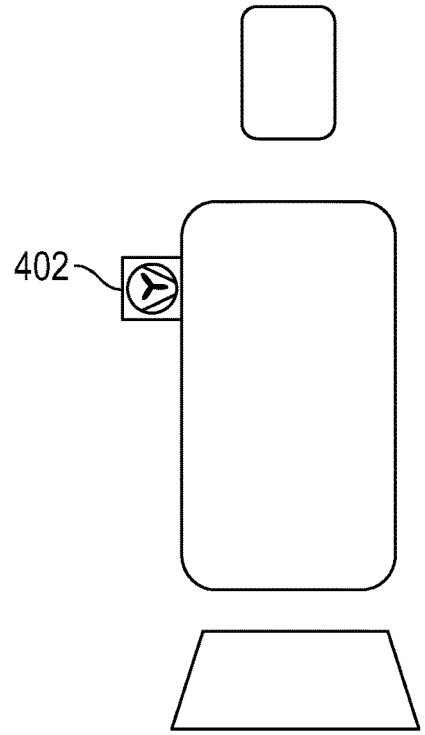
FIG. 6D　　　　FIG. 6E 1. Edge Features
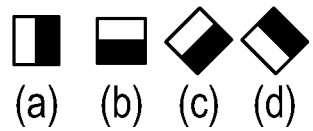
(a)  (b)  (c)  (d)
2. Line Features
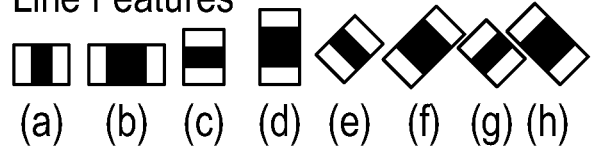
(a)  (b)  (c)  (d)  (e)  (f)  (g)  (h)
3. Center-surround Features
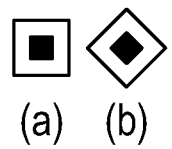
(a)  (b)
FIG. 9
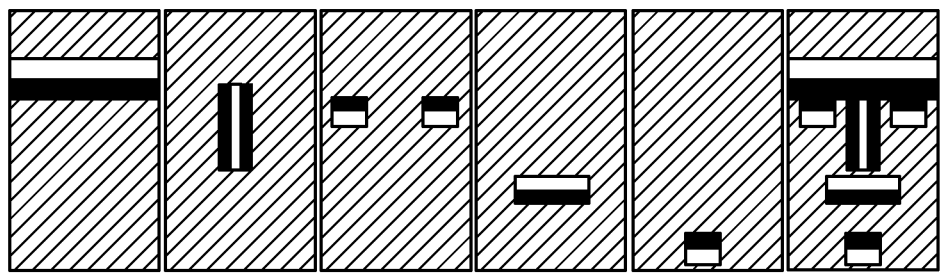
FIG. 10

ROBOT AIR FILTER

CROSS REFERENCE TO RELATED APPLICATIONS

This application claims priority from U.S. provisional patent applications 63/313,317 filed 24 Feb. 2022, 63/327,836, filed 6 Apr. 2022 and 63/483,981, filed 9 Feb. 2023, all of which are incorporated herein by reference.

FIELD OF THE INVENTION

The present invention relates to intelligent robots generally and to a robot with a decontamination filter in particular.

BACKGROUND OF THE INVENTION

Ultraviolet (UV) is a form of electromagnetic radiation with a wavelength from 10 nm[1] (with a corresponding frequency around 30 PHz) to 400 nm (750 THz), shorter than that of visible light, but longer than X-rays.

The table below provides information about types of UV light. The safest and most effective UV frequency used for germicidal purposes is UV-C, and particularly close to 222 nm. One should be careful of old or cheap UV filters that can be made with mercury which can produce toxic ozone as well as dangerous mercury if misused. The Environmental Protection Agency (EPA) currently does not approve or certify any disinfectant UV products. Underwriters Laboratories (UL), however, does certify UV disinfecting products. One of the tests to perform on UV products is the log inactivation test. "Log inactivation" is a convenient way to express the number or percent of microorganisms inactivated (killed or unable to replicate) through the disinfection process. For example, a 3-log inactivation value means that 99.9% of microorganisms of interest have been inactivated.

UV light can be harmful to humans, especially in high amounts, and most commonly comes from the sun. This is why sunscreen is used to protect the skin as well as UV protective sunglasses to protect the eyes. UV light can penetrate cells and affect the DNA/RNA and this can lead to disruption of cell reproduction. Therefore, it can be harmful to viruses, bacteria, and even humans. At the frequency of UV-C, more particularly around 222 nm, UV can easily pierce through viruses and bacteria, but cannot penetrate very far through human skin. Therefore, this frequency is often used in commercial products.

Light-emitting diodes (LEDs) can be manufactured to emit radiation in the ultraviolet range. In 2019, following significant advances over the preceding five years, UV-A LEDs of 365 nm and longer wavelength were available, with efficiencies of 50% at 1.0W output. Currently, the most common types of UV LEDs are in 395 nm and 365 nm wavelengths, both of which are in the UV-A spectrum. When referring to the wavelength of the UV LEDs, the rated wavelength is the peak wavelength that the LEDs generate, and light at both higher and lower wavelength frequencies near the peak wavelength are present, which is important to consider when looking to apply them for certain purposes.

The cheaper and more common 395 nm UV LEDs are much closer to the visible spectrum. LEDs not only operate at their peak wavelength, but they also give off a purple color; and do not emit pure UV light, unlike other UV LEDs that are deeper into the spectrum. Such LEDs are increasingly used for applications such as UV curing applications and charging glow-in-the-dark objects (such as paintings or toys). They are becoming very popular in a process known as retro-brightening, which speeds up the process of refurbishing/bleaching old plastics and portable flashlights for detecting counterfeit money and bodily fluids. LEDS are already successful in digital print applications and inert UV curing environments. Power densities approaching 3 W/cm$^2$ (30 kW/m$^2$) are now possible, and this, coupled with recent developments by photo-initiator and resin formulators, makes the expansion of LED cured UV materials likely.

| Name | Abbreviation | Wavelength (nm) | Photon energy (eV, aJ) | Notes/alternative names |
|---|---|---|---|---|
| Ultraviolet A | UV-A | 315-400 | 3.10-3.94, 0.497-0.631 | Long-wave UV, black light, not absorbed by the ozone layer: soft UV. |
| Ultraviolet B | UV-B | 280-315 | 3.94-4.43, 0.631-0.710 | Medium-wave UV, mostly absorbed by the ozone layer: intermediate UV; Dorno radiation. |
| Ultraviolet C | UV-C | 100-280 | 4.43-12.4, 0.710-1.987 | Short-wave UV, germicidal UV, ionizing radiation at shorter wavelengths, completely absorbed by the ozone layer and atmosphere: hard UV. |
| Near ultraviolet | N-UV | 300-400 | 3.10-4.13, 0.497-0.662 | Visible to birds, insects, and fish. |
| Middle ultraviolet | M-UV | 200-300 | 4.13-6.20, 0.662-0.993 | |
| Far ultraviolet | F-UV | 122-200 | 6.20-10.16, 0.993-1.628 | Ionizing radiation at shorter wavelengths. |
| Hydrogen Lyman-alpha | H Lyman-α | 121-122 | 10.16-10.25, 1.628-1.642 | Spectral line at 121.6 nm, 10.20 eV. |
| Extreme ultraviolet | E-UV | 10-121 | 10.25-124, 1.642-19.867 | Entirely ionizing radiation by some definitions; completely absorbed by the atmosphere. |
| Vacuum ultraviolet | G | 10-200 | 6.20-124, 0.993-19.867 | Strongly absorbed by atmospheric oxygen, though 150-200 nm wavelengths can propagate through nitrogen. |

UV-C LEDs are developing rapidly, but may require testing to verify effective disinfection. Citations for large-area disinfection are for non-LED UV sources known as germicidal lamps Also, they are used as line sources to replace deuterium lamps in liquid chromatography instruments.

UV radiation can generally be contained with opaque materials, such as cardboard or wood. Transparent materials, such as glass, PVC (polyvinylchloride), plexiglass and Perspex, block UV radiation in varying degrees. Generally, carbonated plastics provide adequate UV protection. Some kinds of clear glass (including some kinds of window glass and optical glass) transmit significant amounts of UV-A radiation.

Intelligence robots are known in the art. These robots may be typically autonomous and multi functional and have multiple accessories (such as cameras, speakers, scanners, microphones and sensors). They may use intelligence derived from both artificial intelligence (such as Cloud Artificial Intelligence) or from the processing of operational algorithms such as facial and object recognition, audio recognition etc. to perform their programmed functionality. Intelligent robots are becoming more and more part of everyday life. Such robots are used (for example) for medical care support, as waiters in restaurant, for takeaway deliveries etc.

Personal air purifiers (such as desktop versions and wearable air purifier necklaces) have gained popularity in recent years, especially in urban areas where pollution is high. They can be used to protect against germs, dust, viruses etc. of the immediate surrounding area.

Accordingly, there is a need in the industry and field for a mobile air filter.

SUMMARY OF THE PRESENT INVENTION

To achieve these and other objects, the herein device is a mobile robot with air filters to disinfect local air.

Therefore, to achieve these and other objects, the herein disclosed invention is an intelligent, multi-function robot including: a housing built into the robot and having a UV blocking material, an air filter positioned within the housing; and a fan directing air flow through the air filter, an intake of the airflow and outflow of the airflow through the air filter being placed to direct clean air directed toward a targeted direction. The air filter may be an UV air cleaner/HEPA filter/ionization air cleaner/screen filter. Preferably, the robot is capable of autonomous movement. Additionally, the robot includes means for recognizing a targeted person or direction and means for orienting the robot in relation to the targeted person or direction. The robot may further include multiple fans, tubes and vents, wherein the air flow being blown by the multiple fans via the tubes through a body of the robot out through vents towards a targeted direction. In some embodiments, the air filter can be removably positioned within the robot.

According to a preferred embodiment, the robot further includes a means for identifying the targeted direction. This means for identifying the targeted direction includes: a memory module for the robot containing information about potential targets and identifying characteristics of the potential targets; scanners receiving external information about targets in a vicinity of the robot; and, a processing unit analyzing the external information to identify corresponding identifying characteristics of the potential targets and to then direct clean air toward the target.

In some embodiments, the robot may further comprise means for detecting or tracking targets and means for orienting the robot to face a target. The means for detecting or tracking may include a camera image feed and the means for orienting includes inputs to control the operation of the fan.

There is provided in accordance with a preferred embodiment of the present invention, an intelligent robot. The robot includes at least one accessory to measure activity and state in proximity to the robot, an air filtration module housed in a casing made of a UV blocking material, and a control center to analyze output of the at least one accessory, to recognize a known target user according to the analysis and to control functionality of the robot and the air filtration module for the known target user according to saved preferences for the known target user.

Moreover, in accordance with a preferred embodiment of the present invention, the robot also includes a database to store at least: known target users, air filtration preferences for the known target users and input from at least one accessory, a task processor to perform at least facial recognition on a person in proximity using facial detection and recognition algorithms to determine if the person is a known target user; and a robot controller to orientate the intelligent robot according to the least one accessory and the task processor.

Further, in accordance with a preferred embodiment of the present invention, the intelligent robot also includes an initialization checker to check settings for the air filtration module according to at least one of: default and customized settings; and a mode controller to control the air filtration module according to the results of the initialization checker.

Still further, in accordance with a preferred embodiment of the present invention, the air filtration module includes an air purifier having multiple slots for the addition and removal of at least one air filter; and at least one fan to blow air through at least one airflow tube and out of at least one vent to target the airflow towards the target user.

Additionally, in accordance with a preferred embodiment of the present invention, the air filtration module is removeable from the robot.

Moreover, in accordance with a preferred embodiment of the present invention, the air filter comprises at least one of: a UV air cleaner, a HEPA filter, an ionization air cleaner and a screen filter.

Further, in accordance with a preferred embodiment of the present invention, the at least one accessory is at least one of: a camera, a scanner, a sensor, a microphone and a speaker.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 4A and 4B are schematic illustrations of the front and side of a head-on and cross-sectional view of an air filtration module as integrated into the torso of the intelligent robot of FIG. 1, constructed and operative in accordance with the present invention;

FIGS. 5A-5D are schematic illustrations of a front and side of a first embodiment and a front and side of a second embodiment of an air filtration module mounted as an external module, constructed and operative in accordance with the present invention;

FIGS. 6A-6E are schematic illustrations of various embodiments, showing possible locations for mounting the air filtration module of FIG. 1, constructed and operative in accordance with the present invention;

FIGS. 9 and 10 are schematic illustrations of sample images taken by a camera attached to the intelligent robot of FIG. 1;

Figure 1:
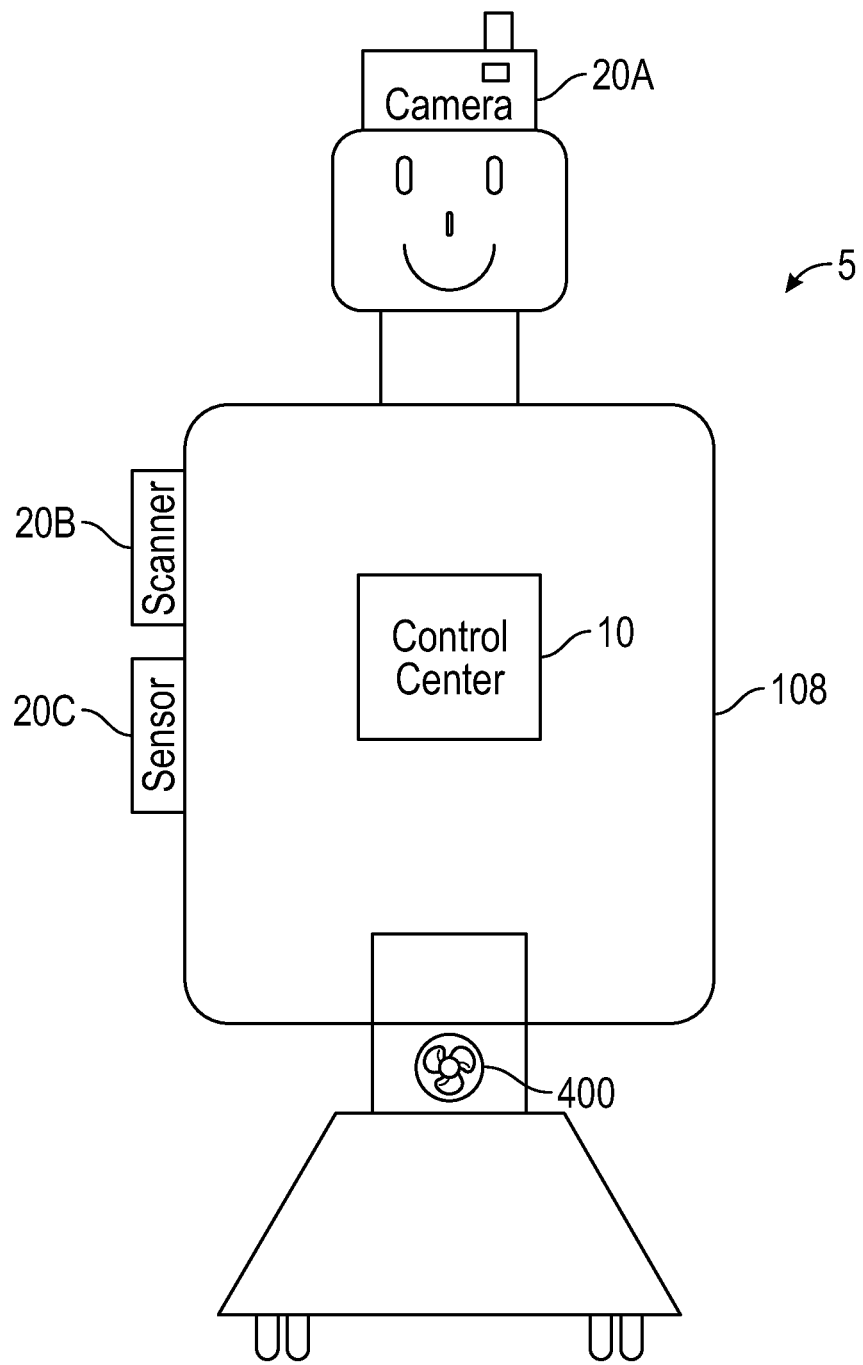
FIG. 1 is a schematic illustration of an intelligent robot having an air filtration module, constructed and operative in accordance with the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicant has realized that an intelligent robot can use navigation, artificial intelligence (AI), audio recognition, image recognition etc. to operate. According to the herein disclosed invention, the intelligent robot comprises an air filtration module and can further operate the air filter using the navigation, AI, audio recognition, image recognition, etc. to take advantage of the systems there to operate the air filter at greater efficiency. A greater efficiency may mean for example using online weather reports or temperature or air sensors to control the operation state of the air filter, alter the operation of the air filter based on whether there are people present and alter the operation of the air filter based on voice command, remote control, mobile app, gesture control or set schedule of a user or target of the robot wherein the schedule of a user can be known through manual input or AI learning. For example, audio commands ("Turn up the fan", "Turn the fan off", "Turn down the fan", etc.) as well as commands from a mobile application (a sliding bar for fan speed, on/off switch, etc.) All these parameters can be customized by the user for each session or can be left at a default setting.

The robot may also use face recognition or voice matching (voice matching is when using voice recognition to recognize an individual based on the sound of their voice) to remember people or match up against a registry of known users which can have different access levels to the control of the intelligent robot or a different priority level and act accordingly. An example of a priority user is a high priority being respiratory patients in a hospital setting.

If multiple people are present, the robot can intelligently operate the air filter to focus on a known user or prioritize users, focus on the closest person if the person is significantly distanced from the intelligent robot, flip focus of the air filter between the users in an interval or periodically, or average the placement of the users and focus at the center if the users are close enough together.

Furthermore, if the air filter further comprises electromechanical equipment like for example a fan and vents then the intelligent robot can operate the electromechanical equipment, for example operate fan speed accordingly, angle vents accordingly.

The intelligent robot may further be able to operate the air filter based on the battery level or charging status. For example, high power operation, normal operation, and power saving operation as well as the basic ON state and OFF state.

Within the robot is a case that encloses an air filter that uses at least one of a known air filter technique like ion filter, screen filter, HEPA filter, UV filter, etc. For the UV filter it must be encased in a UV blocking material like metal or UV blocking plastic. The air flows through the encasing likely with the help of a fan forcing air flow through the filter. The robot has an input vent to intake air placed somewhere on the robot for example near the filter directed toward the floor or directed toward the back of the robot or at an angle between the floor and the back of the robot. The placement is not significant, but it can be beneficial to have the opening near the filter if possible and it can be beneficial to be directed away from the exhaust vent where the clean air will flow out of as to not "steal" the filtered air that is meant for the user.

In a basic embodiment, the invention constitutes a mobile robot with air filters to disinfect local air.

Reference is made to FIG. 1 which illustrates an intelligent robot 5 with an air filter module to disinfect local air for a known target user according to an embodiment of the invention. Robot 5 may comprise a control center 10 to provide and control functionality for robot 5, multiple accessories such as camera 20A, scanner 20B and sensor 20C to measure activity and state in proximity to robot 5 and to provide input to control center 10 and an air filtration module 400. Control center 10 and air filtration module 400 may be housed within a body 108.

Figure 2B:
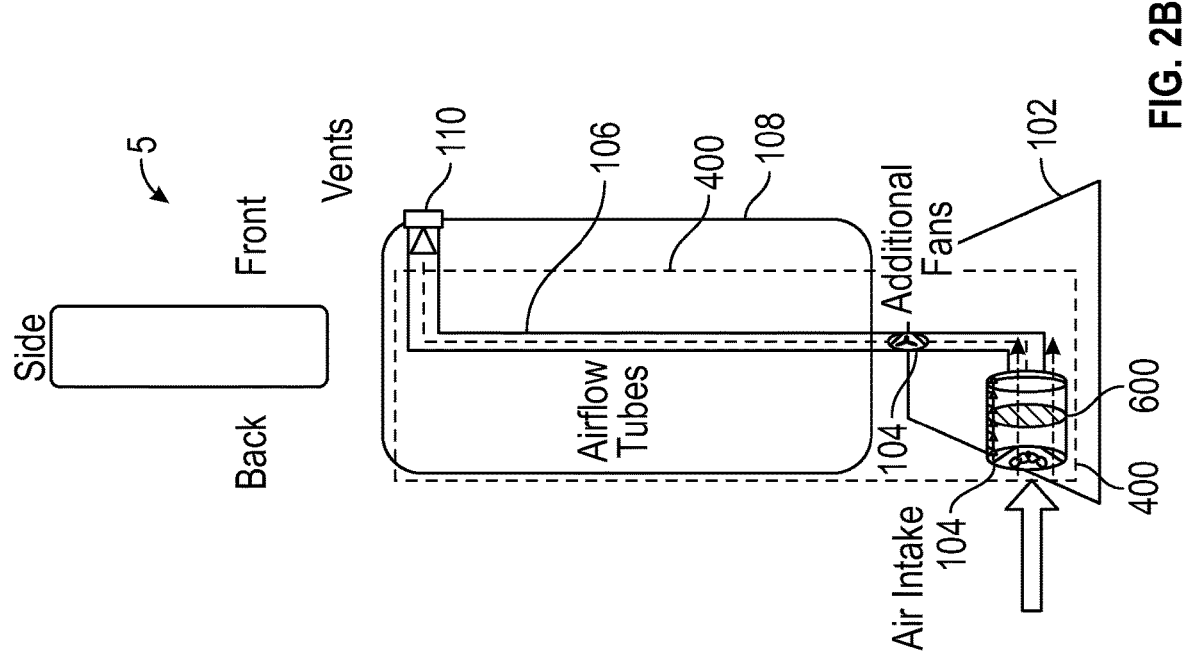
FIGS. 2A and 2B are schematic illustrations of a front and side view of a head-on and cross-sectional view of the intelligent robot of FIG. 1, constructed and operative in accordance with the present invention.
Figure 2A:
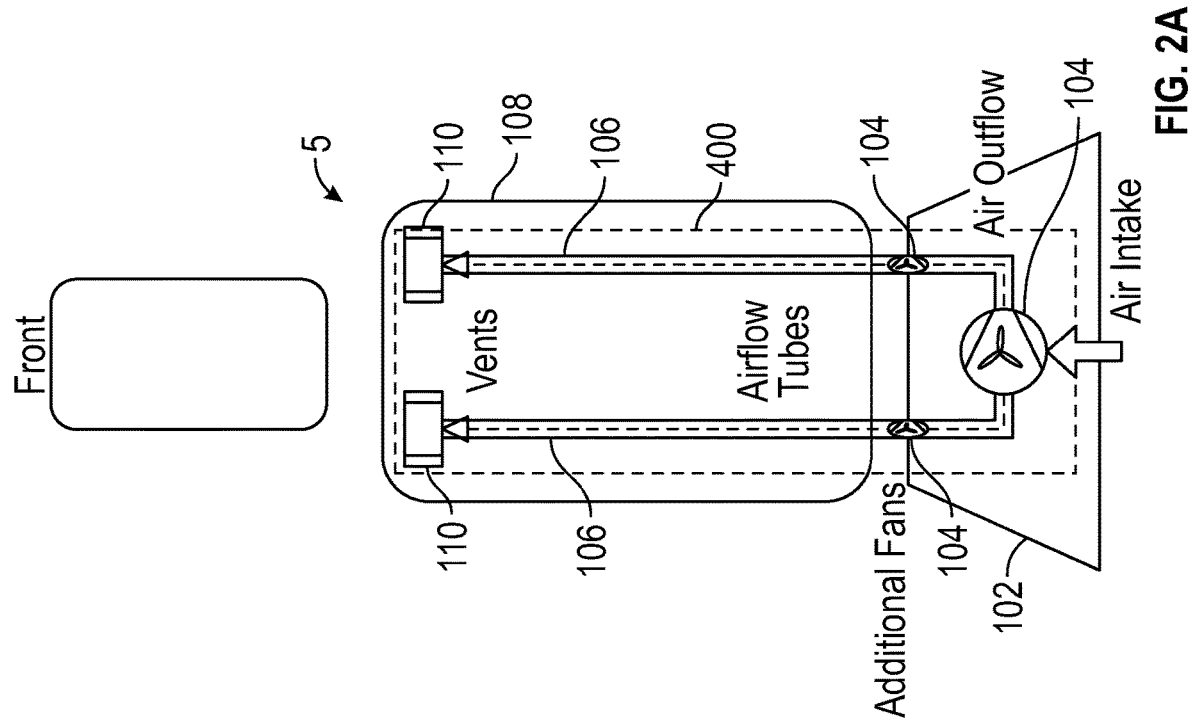

It will be appreciated that air filtration module 400 may comprise an air purifier 600, multiple fans 104, airflow tubes 106 and vents 110 as is illustrated in FIGS. 2A and 2B to which reference is now made. The implementation and function of air filtration module 400 is discussed in more detail herein below.

FIGS. 2A and 2B illustrate solid torso configurations of a head-on and a cross-sectional view of air filtration module 400 as integrated into the body of intelligent robot 5. FIGS. 2A shows a front view of robot 5 and FIG. 2B shows a side view. Both figures show air filtration module 400 integrated in base 102 of robot 5, with air blown out with the help of multiple fans 104 via tubes 106 that pass through the body 108 of robot 5 out through vents 110 towards the user [not shown].

Figure 3:
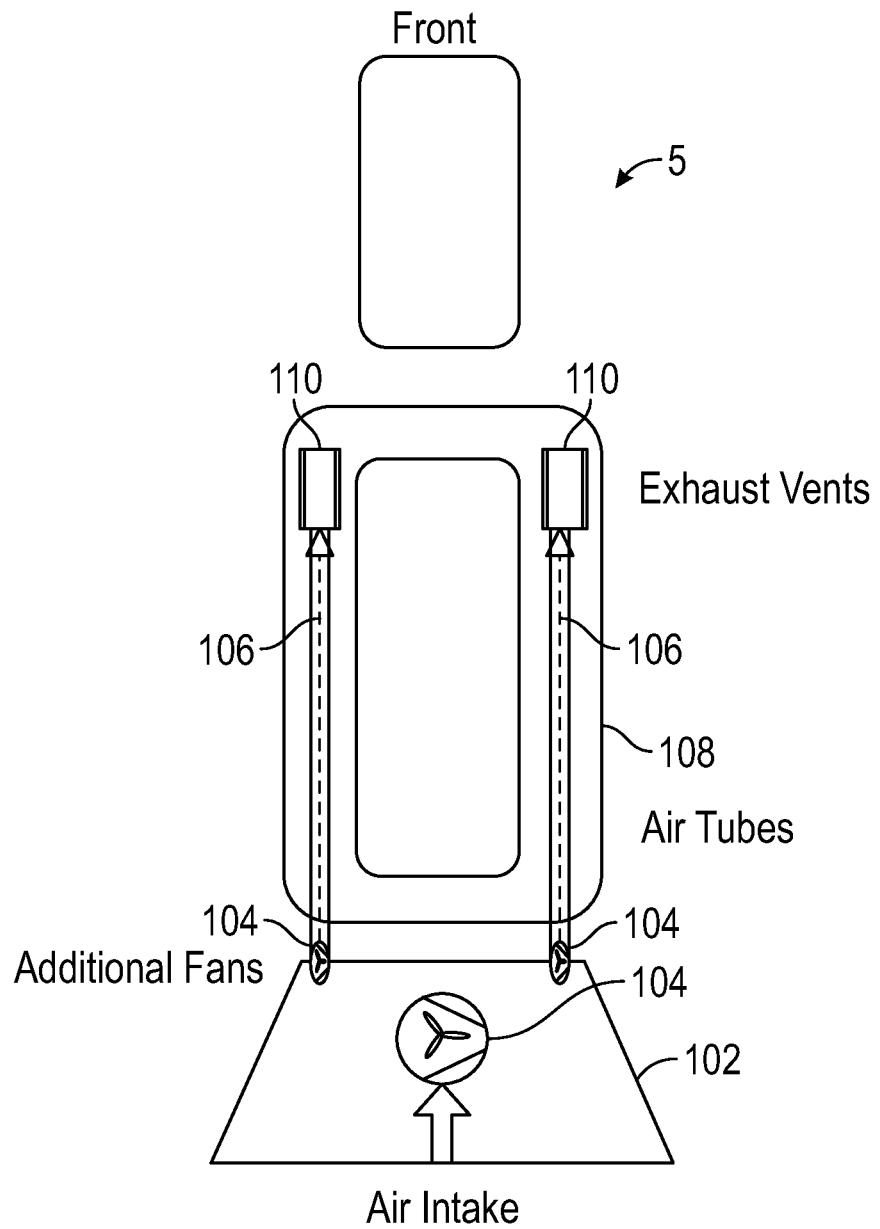
FIG. 3 is a schematic illustration of a head-on view of the intelligent robot of FIG. 1, constructed and operative in accordance with the present invention.

Reference is now made to FIG. 3 which shows an "Hollow Torso Configuration" of a head-on view of air filtration module 400 integrated into a hollow variation of body 108. It will be appreciated that there is no essential difference between this and the solid torso configuration (FIGS. 2A and 2B), except the shape of vents 110 and placement of tubes 106.

Reference is now made to FIGS. 4A and 4B which show a "Torso Mounting" of a head-on and a cross-sectional view of air filtration module 400 as integrated into the torso of intelligent robot 5. In this embodiment, air filtration module 400 is built into the torso, instead of base 102 of robot 5, which may improve airflow. It will be appreciated that air filtration module 400 can be integrated into any part of the body of robot 5.

Figure 5B:
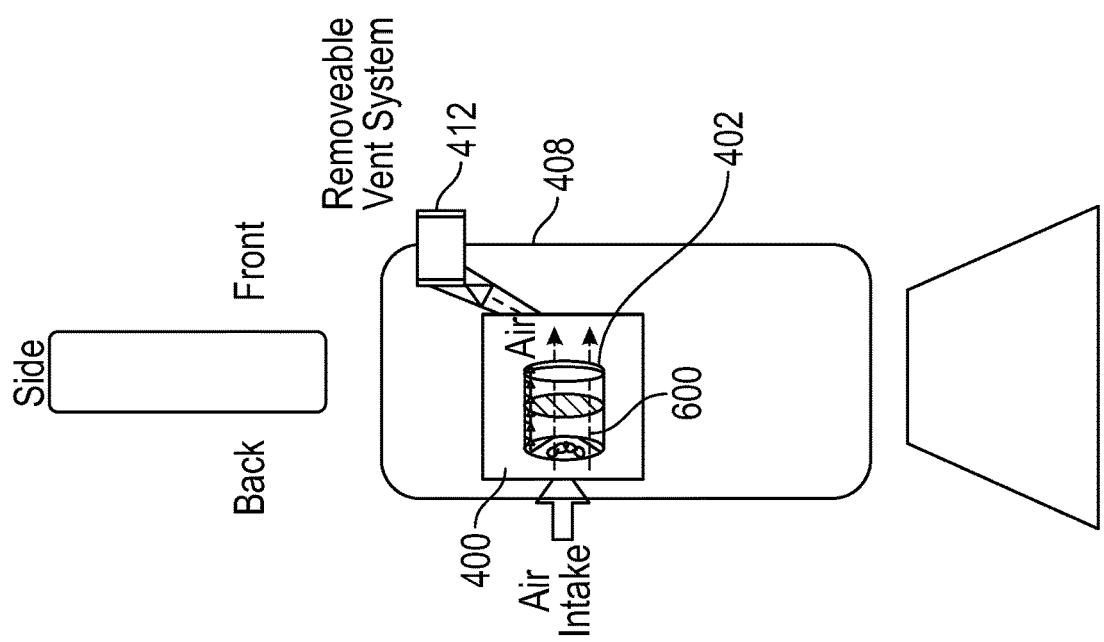
Figure 5A:
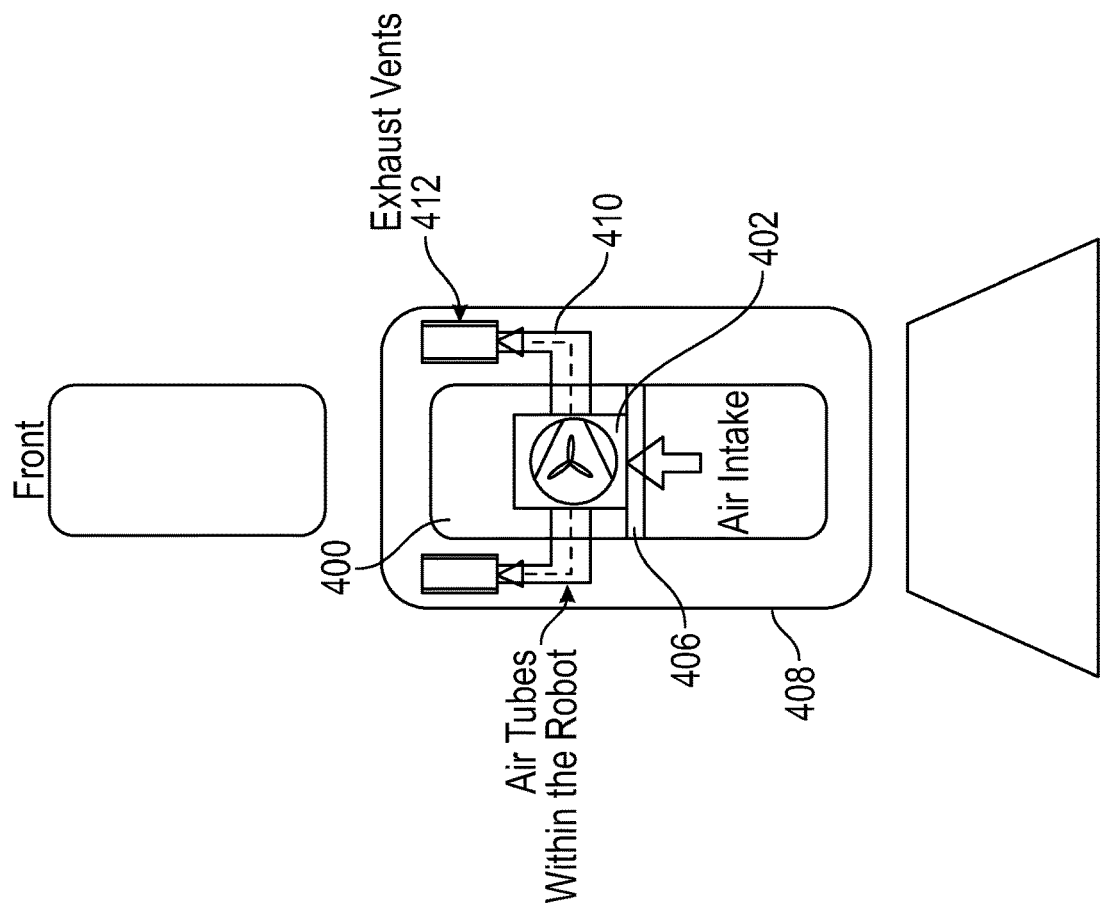

Reference is now made to FIGS. 5A and 5B which show the front and side of a first embodiment and FIGS. 5C and 5D which show the front and side of a second embodiment of a filtration module 400 mounted as an external module 402 on robot 5. They show a "Mountable Module" as an example of a subset of air filtration module 400 mounted as an external module 402 on robot 5. In this embodiment, external module 402 comprising air purifier 600 and a fan or fans 104 is mounted on a shelf 406 in the middle of the robot's torso 408, and airflow is directed through tubes 410 and out through vents 412, all of which are external to the robot's body. It will be appreciated that FIGS. 5A-D illustrate the modularity of air filtration module 400. Robot 5 may have a built-in vent system as shown in FIG. 5C and an aperture 415 in which external module 402 can be inserted and removed, like a cartridge.

Reference is now made to FIGS. 6A-E which show examples of the different locations that external module 402 may be mounted on robot 5.

Figure 7A:
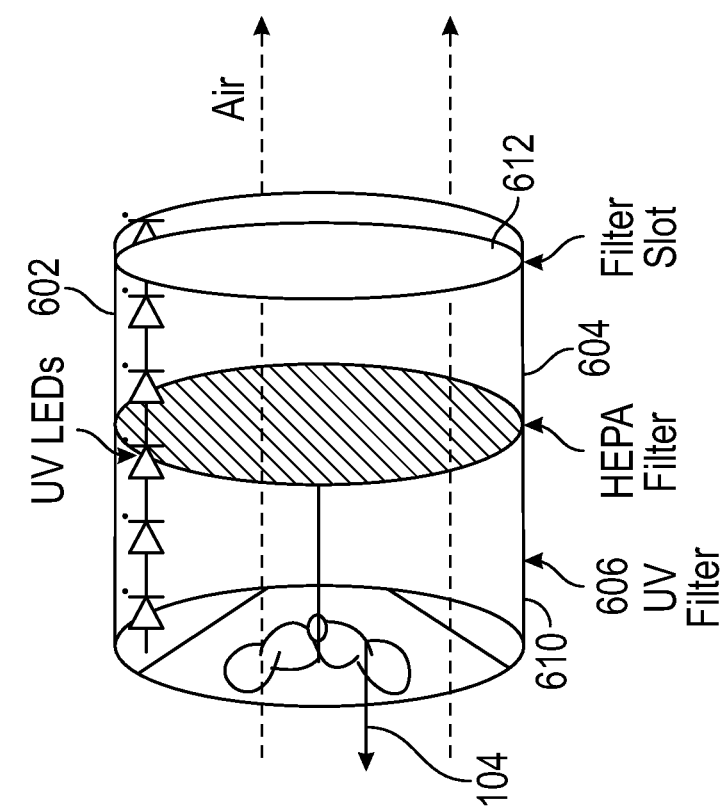
FIGS. 7A and 7B are schematic illustrations of the cross-section of the air purifier of the air filtration module of FIG. 1 with UV LEDs, a HEPA filter, and a UV filter, constructed and operative in accordance with the present invention.
Figure 7B:
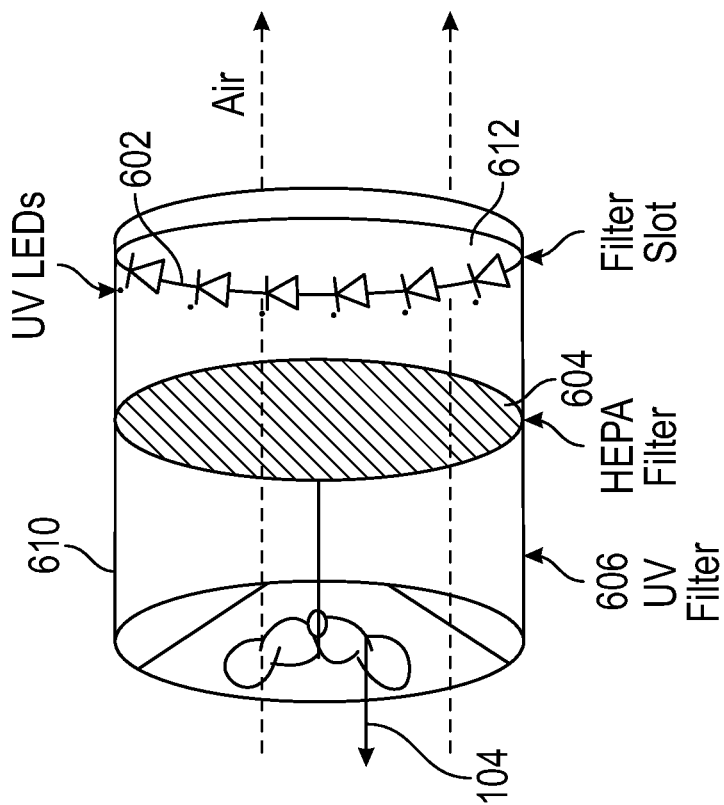

Reference is now made to FIGS. 7A and 7B which illustrate air purifier 600. FIGS. 7A and 7B show a cross-section of air purifier 600 with UV LEDs 602, a HEPA filter 604, a UV filter 606, and fan 104. Air purifier 600 may also contain additional slots 612 for the insertion of additional filters. In FIG. 7A, UV LEDs 602 are integrated onto the inside of casing 610 along rows. FIG. 7B shows UV LEDs 602 being integrated into slots 612.

In a preferred embodiment, air filtration module 400 is attached to robot 5 instead of integrated. This module may be situated in the base of robot 5 or along the sides of robot 5 or as an additional module attached to robot 5

Air purifier 600 may preferably comprise at least one of a UV air cleaner/HEPA filter/ionization air cleaner/screen filter or known air filtering method. If air purifier 600 comprises a UV sub air filter, then the UV air filter is housed within a UV-blocking material which may be, for example, a UV-safe plastic to keep people and the robot safe from the negative effects of the UV light. This will allow people to be in the same room as the UV air cleaner. As discussed herein above module cartridge 402 may be removable so that any filters contained within can be cleaned or replaced when needed which may help for cleaning and repair purposes. As discussed herein above, purifier 600 may be a slot filter system and have designated slots 612 so additional filters can be added, removed, or changed. Reference is now made back to FIG. 5D which shows module cartridge 402 in aperture 415.

It will be appreciated that the slots of purifier 600 may be universal so that any one of the above-mentioned types of filters (UV, HEPA, ionization, etc.) can be inserted or removed at the user's discretion. There can be several of these slots in a single module, with each slot containing either its own unique type of filter or a duplicate of a filter contained in another slot or no filter. This can result in customizable functionality where the user can select several different types of filters to put into the slots of a single module. Alternatively, or in tandem with multiple types of filters, multiple of the same type of filter can be placed into the slots, enhancing the performance of that type of filtration for that module. The slots will allow for ongoing removal and insertion of filters so that filters can be replaced (with the same type of filter that was already there), changed (to a new type of filter), added (if no filter was there before), or removed.

When adding a filter to air purifier 600, the user securely places the filter into filter slot 612. The filter may snap into place when inserted. When removing a filter, whether for the purpose of replacing the filter with another filter of a similar type or a different type or for removing the presence of a filter entirely from that slot, the user will slide the present filter out of the slot before inserting any new filter into the slot. There may be a snap or push-to-release mechanism for removing the filter.

Air filtration unit 400 may comprise one or more fans 104 placed to direct air flow through the air filter. Fan or fans 104 may blow air from outside robot 5 into air purifier 600. Filtered air is blown out of one or more vents towards users, potentially with the help of pipes and additional fans. Robot 5 may maneuver to direct the outflow of air from air purifier 600 towards the user. It will be appreciated that robot 5 can face a user with the use of image recognition and/or voice recognition as described in more detail herein below. Image recognition (recognition of persons, faces, and position) relates to images being received from one or more cameras or scanner mounted on robot 5 are sent to a central processing unit (CPU) such as control center 10 that runs an algorithm on the data that detects the position of any human body in the images. Depending on the position of the body, control center 10 may send commands to the robot's motors to orient robot 5 towards the body. The position of the vents may also be adjustable, both manually and via electronic command, to meet users' preferences. The above example of image recognition applies to the example of audio recognition (recognition of voice matching, direction of arrival (DOA), and natural language processing (NLP).

The presumed shape and structure of air purifier 600 is a UV blocking casing 610 and air filter with openings at opposing ends to allow air flow through casing 610. Air purifier 600 comprises an outside and an inside where UV producing devices, for example UV LEDs 602, are facing inwards on the inside. There may be multiple rows of UV LEDs all around the inside of air purifier 600. Air purifier 600 may be lined on the inner side of the air filter casing 610 (placed along rows or columns) or alternatively can be a part of the filter slot system placed on the inner side of the filter slot. As discussed herein above, air filtration unit 400 may include a fan 104 to direct airflow through air purifier 600. Fan 104 can be placed separate from the casing 610 housing air purifier 600 or be attached to an open side of the air purifier 600 or housed within casing 610 housing air purifier 600. In accordance with the invention, air purifier 600 may have a HEPA filter and/or a screen filter and/or an ionic filter attached to it to filter the air. Air purifier 600 may have designated slots to enable easy entry and removal of these filters. The air intake can be from a set point that may maximize airflow into the filter and/or placed in an opposing direction to the user. For example, it may be placed in the base close to the floor on the back. The air outflow can be from a set point that may maximize cleaned airflow toward the user, such as horizontally placed alongside the front of the torso.

Figure 8:
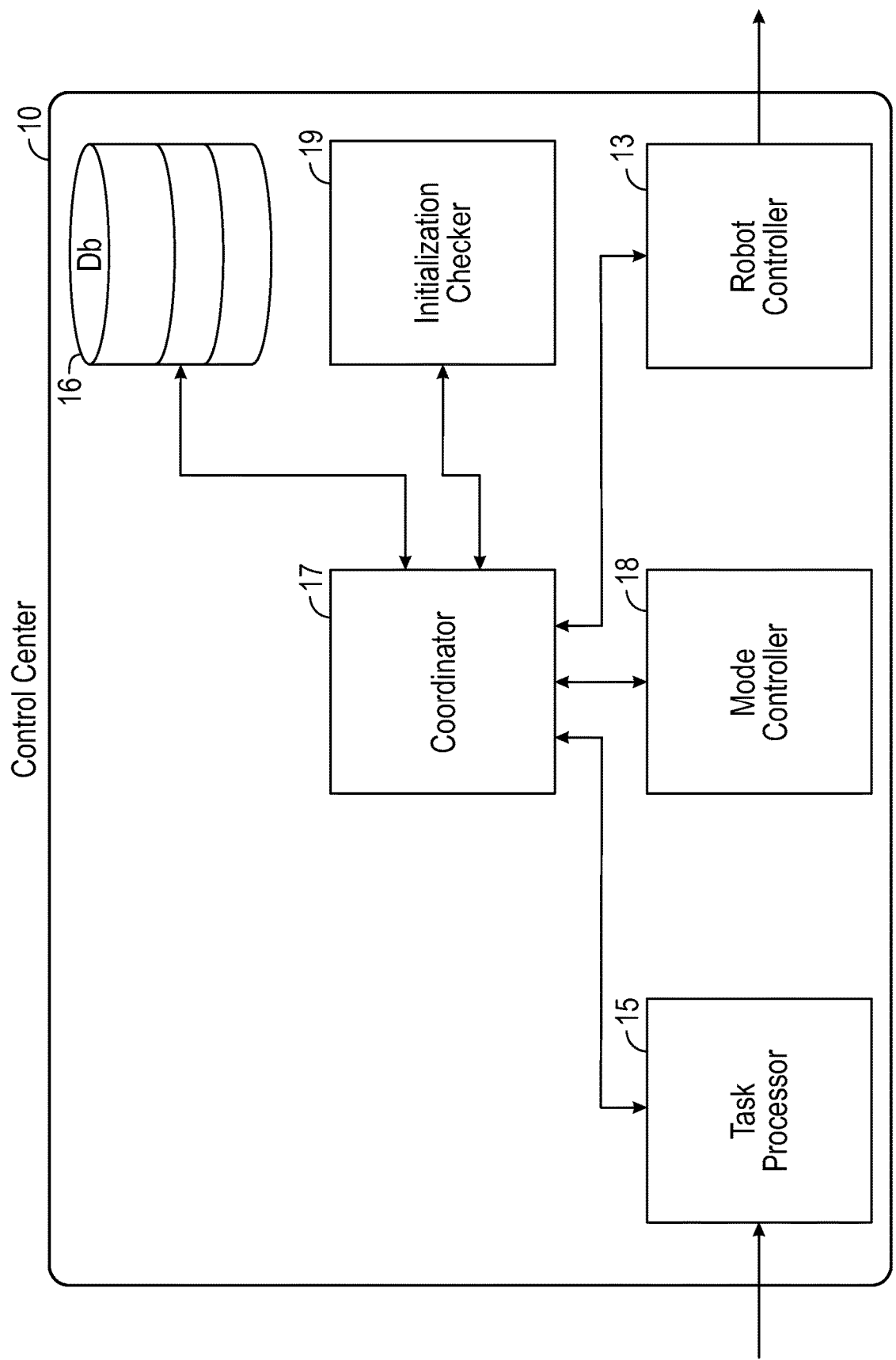
FIG. 8 is a block diagram of the elements of the control center of FIG. 1, constructed and operative in accordance with the present invention.

Reference is now made to FIG. 8 which illustrates the elements of control center 10 which may provide the functionality of facial recognition and other operations for robot 5. It will be appreciated the control center 10 may provide the ability for robot 5 to detect and track known users, orientate robot 5 accordingly and also provide preferences and instructions for directing clean air towards a targeted user.

Control center 10 may comprise a task processor 15, a database 16, a coordinator 17, a mode controller 18, an initializer checker 19 and a robot controller 13.

It will be appreciated that task processor 15 may be equated with the control unit as described in US Patent Publication No. US 2022/0347859 entitled "Robotic Device for Distributing designated items" published 3 Nov. 2022 and granted Jan. 31, 2023 as U.S. Pat. No. 11,565,425, commonly owned by Applicant and incorporated herein by reference. U.S. Pat. No. 11,565,425 describes a control unit for autonomously moving robot 5 through a premise and the use of optical recognition scanners and algorithms to scan a person, to match a scan to a user in its memory and to dispense user medicinal requirements according to a recognized user. Task processor 15 may provide the same capability i.e. user or target recognition and air filtration preferences accordingly as described in more detail herein below.

Database 16 may be a memory storage and store information required to support task processor 15 such as audio data, navigation data and facial recognition data as well as information about user preferences for controlling air filtration module 400. Mode controller 18 may control the different modes of robot 5 according to the output of external and internal influences and the output of task processor 15. Initialization checker 19 may perform initialization checks on robot 5 before it is used. Robot controller 13 may orientate robot 5 according to proximity of users using object and facial recognition analysis and also according to audio data according to task processor 15. Coordinator 17 may coordinate between the different elements of control center 10.

As discussed herein above, robot 5 may use facial recognition to learn to recognize a set of faces by taking multiple pictures of a user's face and running an algorithm that extracts key data about the face, such as eyes, lips, and nose position, and stores the data. Images may be taken via camera 20A and then sent via wired or wireless connection to control center 10 and task processor 15 may run the relevant algorithms and database 16 may store the data. The algorithms may comprise, but are not limited to an initial filtering phase, such as a Haar classifier, which breaks down images to core features like edge and lines as is illustrated in FIG. 9 to which reference is now made. If the groupings of the features seen in the image match human facial features, such as eyes, nose, mouth, and chin, then a face is detected as is illustrated in FIG. 10 to which reference is now made.

Once a face is detected, task processor 15 may perform a more computationally intense analysis where the face is broken down into distinguishable landmarks, which can include, but not limited to, distance between eyebrows, skin color, eye color, nose length, and chin size. These landmarks are then saved to database 16. This process of facial detection and learning is repeated with multiple users to build a database of known user's faces. As robot 5 learns new faces, it can also be taught the specific fan preferences of each user, such as fan speed, distance, UV intensity which also may be saved in database 16. When robot 5 is later asked whether or not it recognizes an unknown user standing in front of it, it takes pictures of the unknown user's face, uses the above-described facial detection and recognition algorithms to extract the facial landmarks, and compares those landmarks to the known faces stored in the database. This comparison is performed by an Artificial Intelligence algorithm such as a Deep Neural Network. If the unknown facial features any of those known users, robot 5 will adjust the fan operation according to that user's preferences.

Figure 11A:
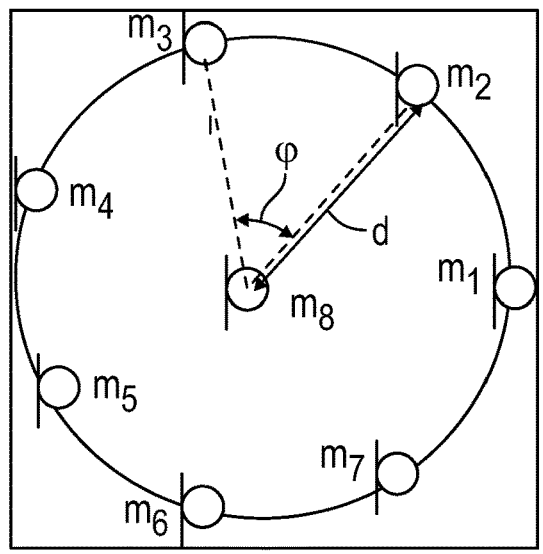
FIGS. 11A-C are schematic illustrations of top and perspective views of possible microphone and camera implementations for the intelligent robot of FIG. 1, constructed and operative in accordance with the present invention.
Figure 11B:
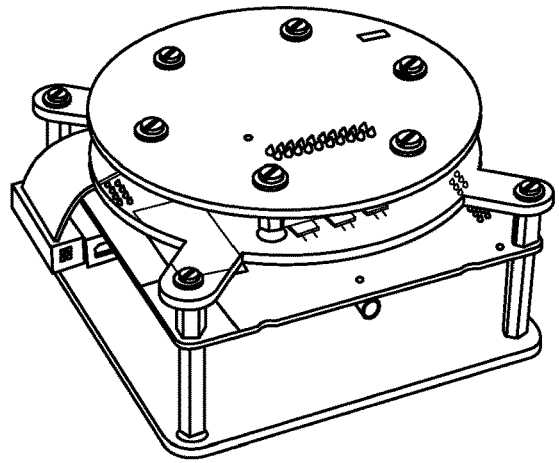
Figure 11C:
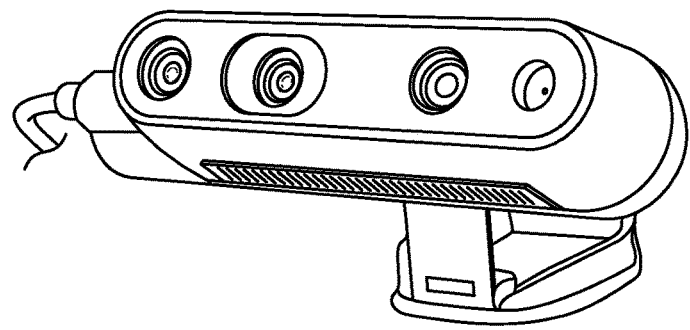
Figure 12:
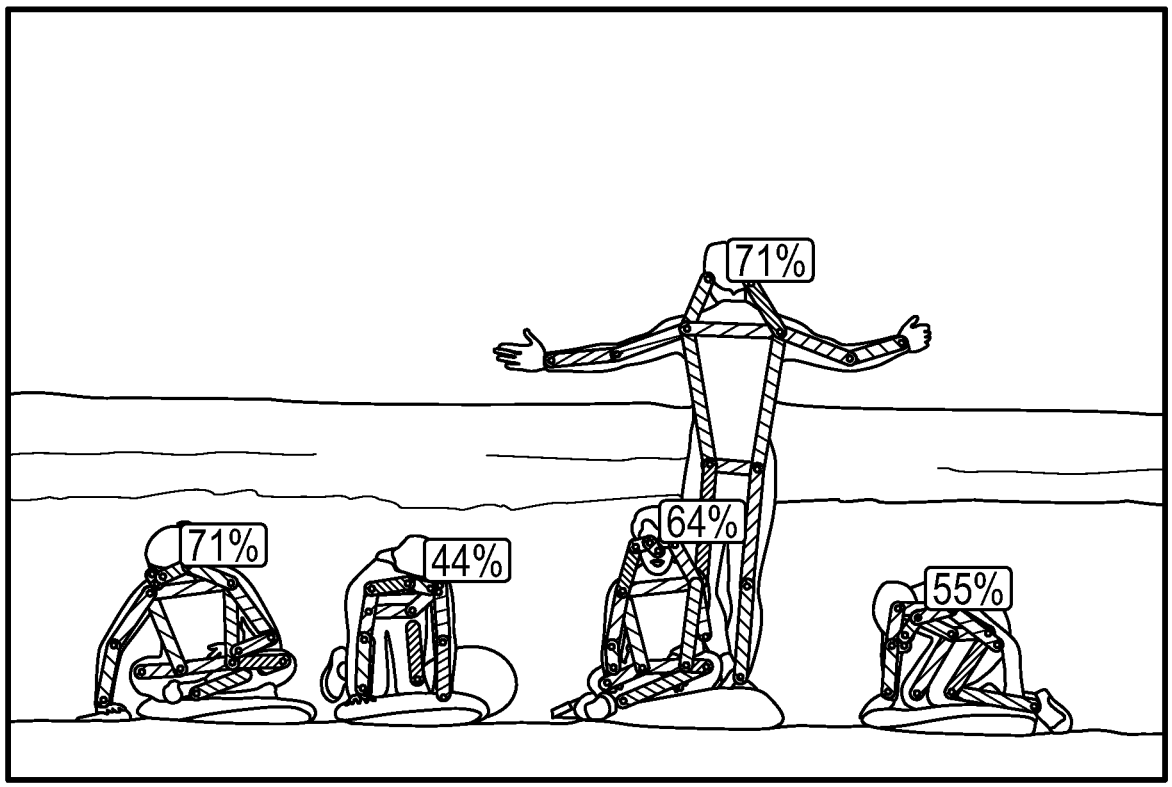
FIG. 12 is a schematic illustration of the detection and tracking of human bodies using the camera image feed of the intelligent robot of FIG. 1.

Reference is now made to FIGS. 11A-C which illustrate possible microphone and camera implementations for robot 5. It will be appreciated that robot 5 may detect and track human bodies in its camera image feed (such as that shown in FIG. 11C). This can be used to orient robot 5 to face the nearest user and then, preferably, blowing clean air directly in his or her direction. Robot 5 may also track gestures, such as waving, shoving motions, thumbs up, thumbs down, and "come-here" summoning motion. These motions can be used as inputs to control the operation of fan 104. For example, "Come here" will indicate to robot 5 that the user wants robot 5 to move closer and blow clean air more directly onto the user. A thumbs up can indicate that the user wants robot 5 to turn up the fan speed, while a thumbs down can mean turn down the fan speed. A shoving motion can indicate to robot 5 to turn away from the user or to back up. Images from cameras 20A may be analyzed by a pose-recognition algorithm that recognizes human figures and returns coordinates (X,Y) or possibly even (X,Y,Z) representing the locations of various key points (such as but not limited to joint locations, center of mass, etc. as illustrated in FIG. 12 to which reference is now made.)

It will be appreciated that one or more of these key points, such as center of mass, is utilized by an algorithm that controls the robot's motors, thereby orienting robot 5 until the key point's coordinates indicate that human figure is in the center of the robot's frame and, therefore, that robot 5 is facing towards the human figure. For example, if the bottom left corner of robot 5 camera frame is at the (X,Y) coordinate (0,0), the top right is at (200,200), and the center of the camera frame is at (100,100), Then, if a person's center of mass is reported at point (150,100), this indicates that the person is to the right of robot 5. Robot 5 will then send a command for its motors to turn clockwise by activating its left wheel. In consequence, robot 5 may turn as such until the center of mass reaches a location that is satisfactorily close to the center of the image frame, like (105,100). The key points are also used to recognize gesture inputs from users. Body gestures can be defined for robot 5 according to parameters such as distance and angles between joints. Task processor 15 may use Artificial Intelligence algorithms such as an Artificial Neural Network to determine if the relationships between the key points it sees on screen matches any of the defined gestures. When such a gesture is recognized, robot 5 will respond accordingly as described herein above.

Robot 5 may also use audio data to turn towards any user that is speaking such as the microphone array shown in FIGS. 11A and 11B back to which reference is now made. This may be achieved by using a circular array of microphones, each reporting its location on the array. They pick up audio information from the environment and report it together with the location data to a computer processing unit. A filter may or might not be applied to eliminate background noise. Task processor 15 may determine which of the microphones in the array is picking up the loudest sound or picked up the sound first (i.e., closest to the origin of the sound), which indicates that the origin of the sound is in the direction of that microphone. Robot controller 13 may then activate its motors to turn towards the origin of the sound until the microphone picking up the loudest audio is that in the center of the array, indicating that robot is facing the origin of the sound.

As discussed herein above, within robot 5 is a case that encloses an air filter module that uses at least one of a known air filter technique like ion filter, screen filter, HEPA filter, UV filter, etc. For the UV filter it must be encased in a UV blocking material like metal or UV blocking plastic. The air flows through the casing 610 likely with the help of a fan 104 forcing air flow through air purifier 600. Robot 5 may have an input vent 110 (as is illustrated in FIGS. 2A and 2B back to which reference is now made) to intake air placed somewhere on robot 5 for example near air purifier 600, directed toward the floor or directed toward the back of robot 5 or at an angle between the floor and the back of robot 5. The placement is not significant, but it can be beneficial to have the opening near air purifier 600 if possible and it can be beneficial to be directed away from exhaust vent 412 where the clean air will flow out of as to not "steal" the filtered air that is meant for the user.

The placement of exhaust vent 114 may be directed toward the front of robot 5 so, when facing a person, the filtered air will be directed toward said person. Technically, if robot 5 has a further improvement and cannot just tilt its head, but also pan its head from side to side or even fully rotate the head, then the air vent will not just simply be in the front, but at a set point or angle that is known to robot 5 prior to operation. For a simple example, if the front of robot 5 is at an angle theta and exhaust vent 412 is facing toward the front of robot 5, then it can be viewed as 0°; and, if robot 5 knows its head is facing at an angle away from the front of robot 5, then it knows the position of what robot 5 sees and where its body is positioned in relation to the body and can face the exhaust vent accordingly. For example, if the robot's head is panned 35° away from the front of robot 5 and it sees a user directly in front of the robot's head, then robot 5 will need to rotate its body 35° in order to face the user. Other known coordinate systems and calculations may be used to achieve similar effects.

At the end of exhaust vent 412 there may be a simple output opening or a manually controlled or electrically controlled or both manually and electrically controlled directional air flow controller controlling the air flow vertically, horizontally, or both vertically and horizontally.

It will be appreciated that air purifier 600 can be placed to be easily removable from robot 5 for cleaning and repair purposes.

Alternatively, air purifier 600 can be an individual module separate from the main body of the robot 5 and be attached to robot 5 at a set point or a number of set points. The set point or number of set points may comprise an electrical connection for power, data, or power and data to connect air filtration module 400 to robot 5. If the air filter is a module, it may comprise all the components on its own or have some components on the main body of robot 5 being partially integrated onto robot 5.

As discussed herein above, a modular constructed robot may include an air filtration module 400. This module may completely self-contain the air filter from air flow input to air flow output, regardless of the other modules making up the modular robot and comprise airflow tubes 106, multiple fans 104 and air purifier 600. It may also be possible to have air purifier 600 partially integrated into another module. For example, there can be a torso module in robot 5, comprising a vent system used by air purifier 600, with a connection point for an air filtration module 400 comprising the air filter's core components (such as, the casing, the filter(s), the vents, pipes). Air filtration module 400 may be attached or removed from the torso module in a cartridge like external module 402 on the modular robot or on the torso itself. Robot 5 can thus function with or without air filtration module 400 attached.

According to the broadest concept of the invention, the core component of air purifier 600 may be defined as filtration module 400 itself. Other components, like the casing, the filters, the fan, the pipes and vents, may not be core components per se, but as preferable or desirable components.

It will be appreciated that the "cartridge like system" 402 may be thought of as analogous to a radio cassette player. The radio cassette player is analogous to the intelligent robot, the radio is analogous to other non-air filter features the robot provides and the cassette player is analogous to the connection components to air purifier 600.

A cassette is analogous to air purifier 600 or air purifier 600's core components. A cassette being able to play different music is further analogous by air purifier 600 being able to be attached to robot 5 and still comprise different internal components like screen filter and/or HEPA filter and/or ion filter and or UV filter etc. Each component individually can have variations in quality and grade thus there can be a plethora of different filters like there are a plethora of cassettes with different music and combinations of songs on it.

A radio cassette player with a cassette inside is also analogous to an intelligent robot comprising a modular air purifier 600 that is able to provide the additional air purifier 600 feature.

The radio cassette player can operate the radio just fine with or without a cassette inside as well as still has all the functionality to play a cassette. But, when a cassette is in the radio cassette player, the radio can in addition play the cassette. A further analogy is the fact that cassettes can play different music.

Figure 13:
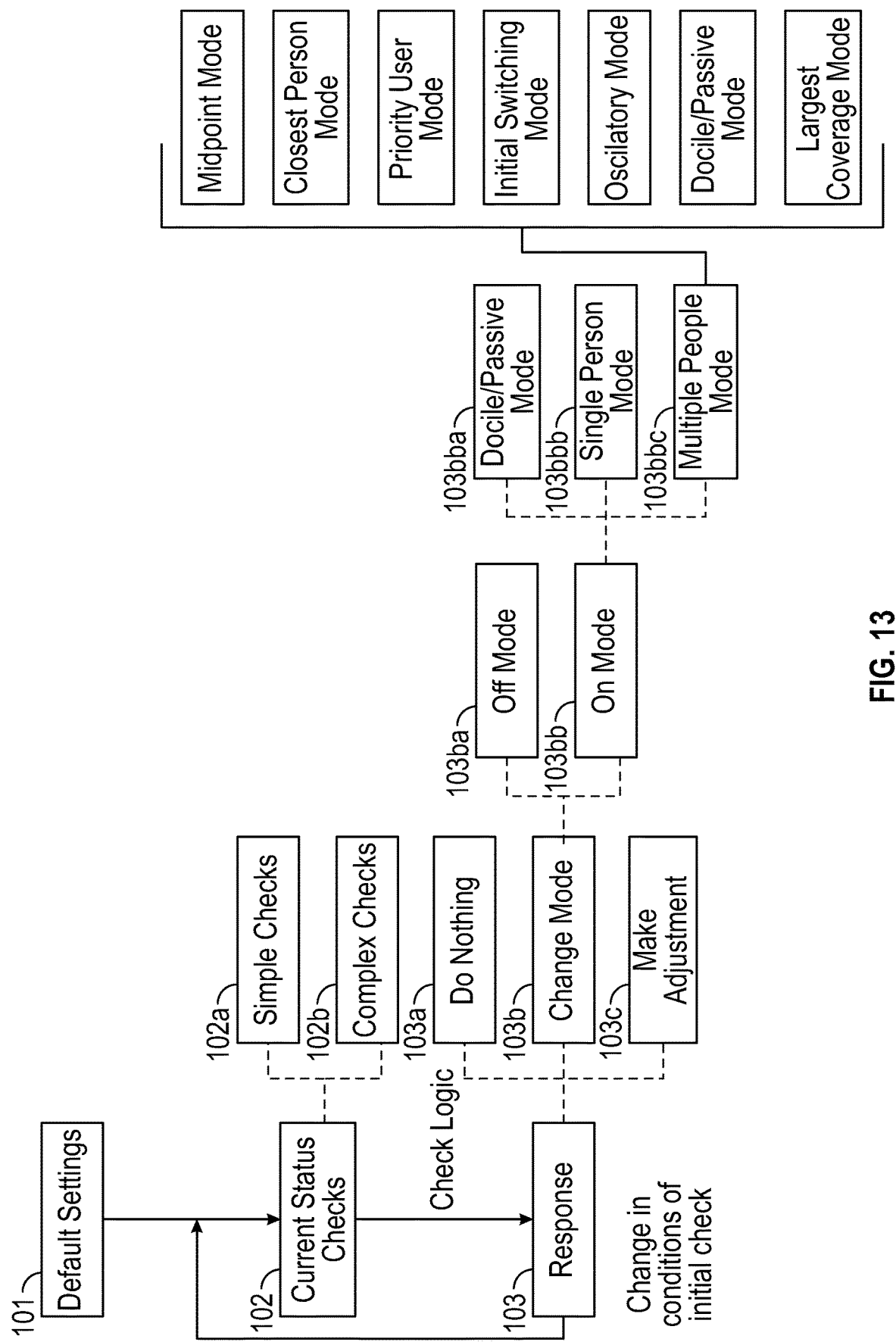
FIG. 13 is a flow chart showing the different mode operations for the air filtration module of FIG. 1, constructed and operative in accordance with the present invention.

Reference is now made to FIG. 13 that shows a flow chart of the different mode operations for air filtration module 400. When robot 5 is activated and the robot turns on, initialization checker 19 may check the air filter default settings or customized default settings (101). The default settings may be congruent air purifier 600 operation logic. These settings may include, for example, air purifier 600 being on at all times, a set battery level, or a charge condition to turn on or off according to a schedule on when to be on or when to be off, etc. After the default settings are checked, initialization checker 19 may make further checks if the current status of robot 5 warrants a response (102). This can include for example, without limitation, internal statuses and external statuses. Examples of current status checks may be the following or a change in status of the following: current battery status, charging status, weather status, person present in robot's vicinity, multiple persons present in the robot's vicinity, command given to robot 5, a set of time allotted past, a signal from the robot's AI, a scheduled event occurs, default setting have changed, default setting conditions were triggered, image recognition status, voice recognition status, robot person interaction status, robot current activities and current priority list of activities status, etc. Any other relevant status can also be monitored.

The current status default checks 102 may be further broken down into simple current status checks 102*a* and complex status checks 102*b* and may comprise even further levels, dividing the checks on computational means like time, CPU usage, memory, etc. This may be done to allow robot 5 to preform simple checks first before the complex checks. For example, if the robot 5's battery is under a set level, for example 2%, then robot 5 may be set to operate the air purifier 600 in the off mode and no longer requires more complex checks to determine the status of air purifier 600.

Mode controller 18 may use logic to determine if the results of the checks warrant a response determined by default settings or customized default settings.

It will be appreciated that there are 3 archetypal responses 103 that mode controller 18 may choose: do nothing 103*a* (do not make any changes), change mode 103*b*, or adjust within the current mode 103*c*. If the mode controller 18's response is 103 is do nothing 103*a*, air purifier 600 will remain in the current state and current mode of operation. When the robot 5 response 103 is in changing mode 103*b*, mode controller 18 may change the operation of air filter mode. For example, changing mode 103*b*, switching from "Midpoint Mode" to "Priority User Mode" will cause robot 5 to switch from directing the air purifier 600 towards the midpoint of detected users to focusing exclusively on a high-priority user. If mode controller 18's response 103 is adjust within the current mode 103*c*, mode controller 18 may adjust the operation of air purifier 600 within its current mode—it will follow the specific behavior protocol dictated by that mode. For example, if while robot 5 is in "Midpoint Mode," a check detects that a user has moved, mode controller 18 may adjust (without changing mode) by calculating a new midpoint between the users it sees and moving to face towards the new midpoint.

The operation mode of air purifier 600 may comprise two general modes, off mode 103*ba* and on mode 103*bb*. Off mode 103*ba* comprises the mode where air purifier 600 is in the off state and on mode 103*bb* comprises the mode where air purifier 600 is in the on state. Within on mode 103*bb*, there are several sub-modes that can further delineate the behavior pattern of robot 5. For example, this may include operation modes like passive mode 103*bba*, single user mode 103*bbb*, and multi-user mode 103*bbc*. Where the operation in passive mode may comprise air purifier 600 in an on state passively active, but not directly targeting a user. Where the operation is in single user mode 103*bbb*, robot 5 may notice a single user and target air purifier 600 at the single user. When the operation is in multi-user mode 103*bbc*, robot 5 may notice multiple users and target air purifier 600 toward at least one of the users. Each of these modes, passive mode 103*bba*, single user mode 103*bbb*, and multi-user mode 103*bbc*, may in part each have further sub-modes. For example, the multi-user mode 103*bbc* mode may operate in a number of sub-modes which may comprise, but not limited to, a midpoint mode, a closest person mode, a priority user mode, an interval switching mode, an oscillatory mode, a passive mode, a largest coverage mode. Wherein, for example, midpoint mode denotes that, when robot 5 detects multiple people, it should face a midpoint between the users. Closest person mode denotes that, when robot 5 detects multiple people, it should only turn to face towards the closest person. Priority user mode denotes that, when robot 5 detects multiple people, it should ignore all humans and only face towards a specific person deemed a priority user. Interval switching user mode denotes that, when robot 5 detects multiple people, it should face each user for a set or variable time interval and switch between them. Oscillatory mode denotes that, when robot 5 detects multiple people, it should move air purifier 600 in an oscillatory manner spanning the coverage of air purifier 600 to the users. Passive mode denotes that, when robot 5 detects multiple people, it should passively be in the on mode in the vicinity of the users. Large coverage mode denotes that, when robot 5 detects multiple people, it should face in a general direction of the largest group or cluster of users to cover the largest number of users. Some of these sub-mode's principles may be altered in some way and may be altered to be operational as subsets for the single user mode 103*bbb* where applicable.

It will be appreciated that the above are just illustrative examples of possible operating modes. Any other suitable mode may be created and utilized.

The protocol for if or when to switch between such modes are all included in the initial settings and can be pre-programmed by the development team, customized for specific user requirements, operated through artificial intelligence, or a combination of any of them. For example, mode controller 18 may shift without any default setting to switch into the "Priority User Mode". However, a particular doctor working in the robot's facility may decide that he or she wants robot 5 to recognize him or her as a priority user. The doctor can modify the robot's settings, so that whenever the results of the robot's status checks show that this doctor is detected, the robot will switch out of its current mode, enter "Priority User Mode", and turn to face the doctor. Thereafter, the robot will stay in this mode until checking results indicate, according to the robot's default settings, that the robot should switch to a different mode. As there are many sub-modes in 103 the logic for when and how to switch between modes can be quite complex, but it will all be performed according to the robot's settings and check results. An example of a combination of pre-programmed by the development team and user customized is if the air filter is pre-programmed by the development team to change to the off mode if the battery is below a set percentage range, say 0-25% battery, and user customizable may be within the range of 5-25%, allowing the user to set the feature as low as 5% or as high as 25%.

Figure 14:
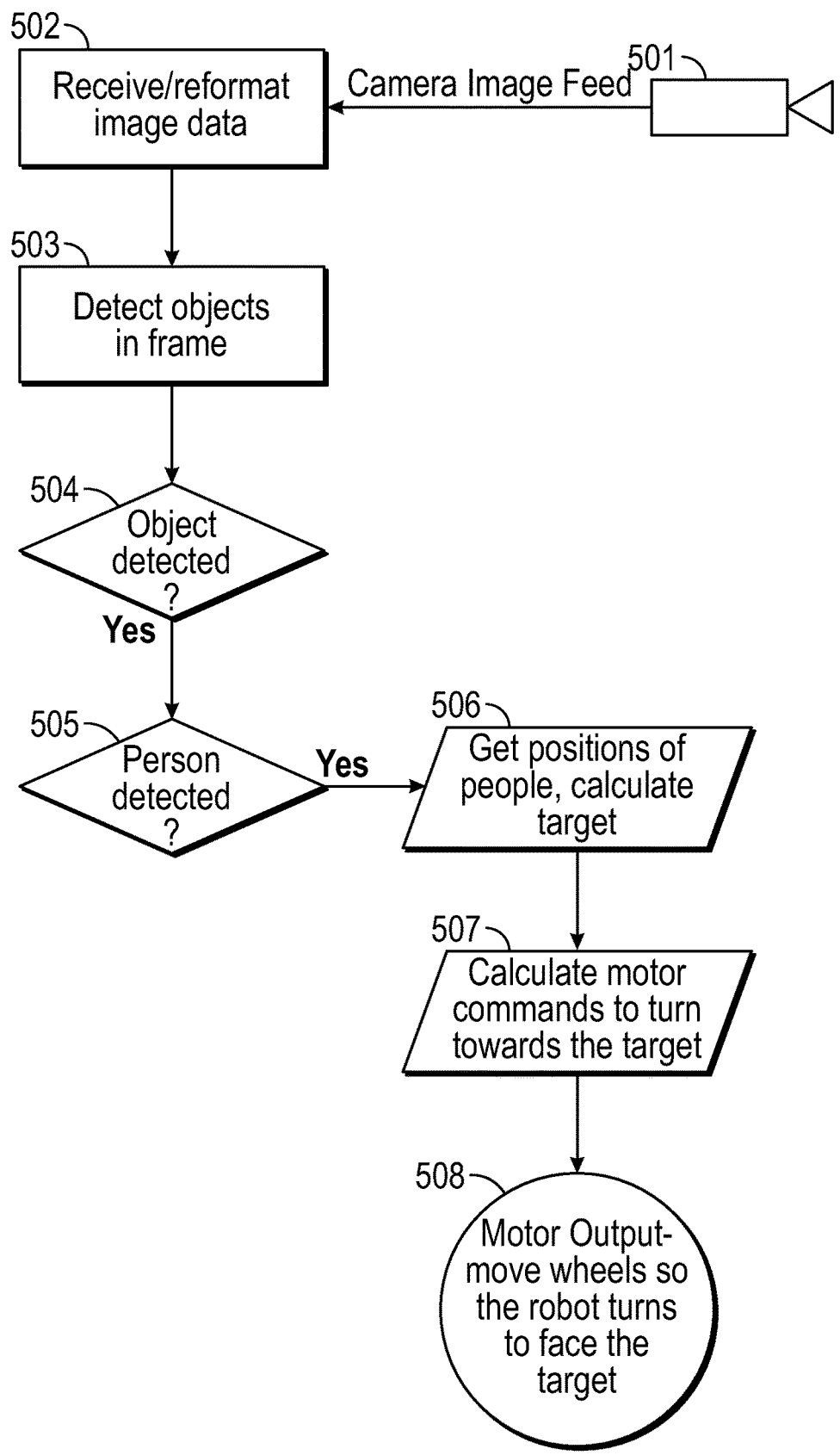
FIG. 14 is a flow chart showing the logical flow for the intelligent robot of FIG. 1 using image processing results to physically turn the robot to face a desired target, constructed and operative in accordance with the present invention.

Reference is now made to FIG. 14 which shows the logical flow for how robot 5 may use image processing results from task processor 15 to generate a motor response in which robot 5 physically turns to face a desired target. The image processing results generate a motor response in which robot 5 physically moves to face a desired target. Initially, a scanner attached to robot 5 scans for an image 501. Task processor 15 may check for any known objects or persons (steps 504 and 505) that it can recognize in the image data 503. If an object is not detected, robot 5 may, for example, have no change in status or switch to the OFF mode. When robot 5 does detect an object, robot 5 may determine if that object is an object of target value, for example the object being a person, pet, etc. Task processor 15 may calculate (step 506) the position of the object of target value and set that value as a marker. This marker may be a target or used to calculate a target or set of targets or area of targets. Thereafter, task processor 15 may calculate the required motor movement (step 507) and then sends a command to robot controller 13, based on the calculated required motor movement, to move toward or angle toward or both move toward and angle toward a target, set of targets or area of targets. At this point (step 508), the motor then executes the command and moves the intelligent robot to face toward a target, set of targets or area of targets.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances, cloud computing units or similar electronic computing devices that manipulate and/or transform data within the computing system's registers and/or memories into other data within the computing system's memories, registers or other such information storage, transmission or display devices.

Embodiments of the present invention may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

Some general purpose computers may comprise at least one communication element to enable communication with a data network and/or a mobile communications network.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A mobile robot suitable for autonomous movement and/or orientation towards a target, the robot comprising:
   a central processing unit (CPU) and a camera suitable for providing an image feed to the CPU;
   a UV radiation resistant housing built into the robot and a UV air filter positioned within the housing and suitable for disinfecting air blown out of the robot as clean air via a fan; means suitable for detecting, tracking and orienting the robot to face the target;
   means suitable for directing the clean air toward the target;
   means suitable for a control center implemented on the CPU identifying the target from the image feed, the means control center comprising a memory module connected to the CPU and containing a database having information about the target used for identifying characteristics of the target;
   the control center navigating the robot to face the target and to continue to face the target as the target moves;
   an air filtration module directing the clean air toward the target;
   wherein;
   the camera provides the image feed to the control center which in turn carries out image recognition from the image feed to identify characteristics to detect a face and, once a face is detected, performs an analysis to identify the detected face by an artificial intelligence algorithm using distinguishable landmarks and learning;
   and wherein;
   by a process of repeated facial detection and learning the memory module database is built and preferences for each target are stored therein;
   if a face is already known to the memory module database the robot can direct control center instructs the air filtration module to direct clean air toward the target(s) according to preferences stored in the memory module database for the target(s);
   and wherein
   by a process of repeated facial detection and learning a database of known users is built;
   and wherein;
   the robot can be taught preferences of known users and store them in the memory module database;
   so that the robot can adjust operation of the fan to the preferences of the target.

2. The robot according to claim 1, wherein said robot further comprising multiple fans, tubes and vents, wherein air flow is blown by said multiple fans via said tubes through a body of the robot out through vents towards a targeted person or direction.

3. The robot according to claim 1, wherein said air filter being removably positioned within said robot.

* * * * *